(12) United States Patent
Park et al.

(10) Patent No.: US 12,310,713 B2
(45) Date of Patent: May 27, 2025

(54) METHOD OF QUANTIFYING MAGNETIC RESONANCE DIFFUSION PARAMETERS BY USING DIFFUSION WEIGHTED MAGNETIC RESONANCE IMAGES

(71) Applicant: Korea Advanced Institute of Science and Technology, Daejeon (KR)

(72) Inventors: Hyunwook Park, Daejeon (KR); Wonil Lee, Daejeon (KR); Jongyeon Lee, Daejeon (KR); Giyong Choi, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 156 days.

(21) Appl. No.: 18/162,016

(22) Filed: Jan. 31, 2023

(65) Prior Publication Data
US 2024/0148267 A1    May 9, 2024

(30) Foreign Application Priority Data

Nov. 9, 2022   (KR) .................. 10-2022-0149013
Dec. 28, 2022  (KR) .................. 10-2022-0187041

(51) Int. Cl.
*A61B 5/055*    (2006.01)

(52) U.S. Cl.
CPC .... *A61B 5/055* (2013.01); *G06T 2207/10088* (2013.01)

(58) Field of Classification Search
CPC ............... A61B 5/055; A61B 5/7264; G06T 2207/10088; G01N 3/00
See application file for complete search history.

(56) References Cited

U.S. PATENT DOCUMENTS

| | | | |
|---|---|---|---|
| 11,937,908 B2* | 3/2024 | Chauffert | G01R 33/4826 |
| 12,064,227 B2* | 8/2024 | Katouzian | G16H 30/40 |
| 2016/0139226 A1* | 5/2016 | Manikis | G01R 33/5608 703/2 |
| 2020/0205692 A1* | 7/2020 | Chauffert | G01R 33/543 |
| 2021/0239780 A1* | 8/2021 | Fan | G06N 3/084 |
| 2021/0365722 A1* | 11/2021 | Masuda | G06N 5/04 |
| 2023/0296711 A1* | 9/2023 | Maier | G01R 33/56341 324/309 |
| 2024/0148267 A1* | 5/2024 | Park | A61B 5/055 |

OTHER PUBLICATIONS

Lee [Registration and quantification network (RQnet) for IVIM-DKI analysis in MRI, 2022 International Society for Magnetic Resonance in Medicine] (Year: 2022).*

(Continued)

*Primary Examiner* — Oommen Jacob
(74) *Attorney, Agent, or Firm* — DALY, CROWLEY, MOFFORD & DURKEE, LLP

(57) ABSTRACT

Disclosed is an unsupervised deep learning method, which simultaneously performs registration between diffusion weighted magnetic resonance images and quantification of diffusion parameters. The unsupervised deep learning method decreases a registration error caused by a contrast difference by comparing a similarity between images of the same contrast, increases the performance of registration, and increases the accuracy of quantifying magnetic resonance diffusion parameters.

10 Claims, 11 Drawing Sheets

(56) References Cited

OTHER PUBLICATIONS

Li [Fast and Robust Diffusion Kurtosis Parametric Mapping Using a Three-Dimensional Convolutional Neural Network, IEEE Access 2019] (Year: 2019).*
Gao [Dynamic Zoom-in Network for Fast Object Detection in Large Images, Computer Vision Foundation 2018] (Year: 2018).*
Bertleff [Diffusion parameter mapping with the combined intravoxel incoherent motion and kurtosis model using artificial neural networks at 3 T, NMR in Biomedicine, 2017] (Year: 2017).*
Bai et al., "Model-Based Registration to Correct for Motion Between Acquisitions in Diffusion MR Imaging;" $5^{th}$ IEEE International Symposium on Biomedical Imaging: From Nano to Macro; May 14, 2008; pp. 947-950; 4 Pages.
Bertleff et al., "Diffusion Parameter Mapping with the Combined Intravoxel Incoherent Motion and Kurtosis Model Using Artificial Neural Networks at 3 T;" Research Article from Wiley NMR in Biomedicine; Accepted Aug. 17, 2017; 11 Pages.
Friston, "Statistical Parametric Mapping;" Chapter 16 from *Neuroscience Databases*; Jan. 2003; pp. 237-250; 14 Pages.
Jalnefjord et al., "Comparison of Methods for Estimation of the Intravoxel Incoherent Motion (IVIM) Diffusion Coefficient (D) and Perfusion Fraction (f);" Research Article from Magnetic Resonance Materials in Physics, Biology and Medicine; Published Online Aug. 16, 2018; 9 Pages.
Jenkinson et al., "FSL;" Journal Article from NeuroImage, 62; Available Online Sep. 16, 2011; 9 Pages.
Lee et al., "Quantification of Intravoxel Incoherent Motion with Optimized b-Values Using Deep Neural Network;" Full Paper from Magnetic Resonance in Medicine; Accepted Jan. 13, 2021; pp. 230-244; 15 Pages.
Lee et al., "Registration and Quantification Network (RQnet) for IVIM-DKI Analysis in MRI;" Research Article from Magnetic Resonance in Medicine; Published Sep. 19, 2022; 35 Pages.
Lee et al., "Registration and Quantificationn Net (RQnet) for IVIM-DKI Analysis;" Presentation Abstract (0556) from the Proceedings of the Joint Annual Meeting ISMRM-ESMRMB & ISMRT Annual Meeting; May 7, 2022; 4 Pages.
Lu et al., "Extension of the Intravoxel Incoherent Motion Model to Non-Gaussian Diffusion in Head and Neck Cancer;" Journal of Magnetic Resonance Imaging, vol. 26; Nov. 2012; 9 Pages.
MRIquestions.com, "DWI b-Value;" Questions and Answers in MRI; Retrieved from https://mriquestions.com/what-is-the-b-value.html on Jan. 24, 2023; 2 Pages.
Vasylechko et al., "Self-Supervised IVIM DWI Parameter Estimation with a Physics Based Forward Model;" Research Article from Magnetic Resonance in Medicine; Accepted Aug. 8, 2021; 11 Pages.

\* cited by examiner

METHOD OF QUANTIFYING MAGNETIC RESONANCE DIFFUSION PARAMETERS BY USING DIFFUSION WEIGHTED MAGNETIC RESONANCE IMAGES

CROSS-REFERENCE TO RELATED APPLICATION(S)

This application claims the priority benefit of Korean Patent Application No. 10-2022-0149013 filed on Nov. 9, 2022, and Korean Patent Application No. 10-2022-0187041 filed on Dec. 28, 2022, in the Korean Intellectual Property Office, the disclosure of which is incorporated herein by reference for all purposes.

BACKGROUND

1. Field

One or more embodiments relate to a method of quantifying magnetic resonance diffusion parameters.

2. Description of Related Art

Diffusion magnetic resonance imaging is a technique for non-invasively obtaining information regarding the inside of a human body by imaging the diffusion of water molecules. The diffusion of water molecules inside the human body may be affected by microstructures, such as cell fibers or membranes, different from diffusion in uniform water. The diffusion magnetic resonance imaging may image the structure of cells or the feature of cells by obtaining information on the diffusion of water molecules. To quantify a degree of the diffusion of water molecules inside the human body, diffusion weighted magnetic resonance images (DW-MRIs) may be obtained and registered with one another, and the registered images may be applied to a diffusion model. A person may inevitably move in a magnetic resonance imaging (MRI) system while capturing DW-MRIs, and the obtained DW-MRIs may accordingly be unaligned with one another. When performing quantification by using the unaligned DW-MRIs, the accuracy of quantification may decrease. Therefore, the DW-MRIs obtained for quantification may necessarily be registered with one another. As such, the accuracy of quantification may depend on the accuracy of registration, and thus, accurate registration between images may be highly important. Typical techniques have attempted registration between DW-MRIs by spatially transforming the DW-MRIs in order to increase a similarity to a reference image after obtaining the DW-MRIs. However, the accuracy of registration in a method of increasing a similarity may decrease when image contrast is highly different between images.

SUMMARY

An aspect provides a method of quantifying magnetic resonance diffusion parameters for increasing the accuracy of quantifying the magnetic resonance diffusion parameters.

The technical goal obtainable from the present disclosure is not limited to the above-mentioned technical goal, and other unmentioned technical goals may be clearly understood from the following description by those having ordinary skill in the technical field to which the present disclosure pertains.

According to an aspect, there is provided is a method of quantifying magnetic resonance diffusion parameters by using diffusion weighted magnetic resonance images. The method may include (i) preparing a reference image and diffusion weighted magnetic resonance images; (ii) controlling the reference image to be input to first neural networks and the diffusion weighted magnetic resonance images to be respectively input to the first neural networks, in which the first neural networks respectively include different first weights, the first neural networks are configured to estimate transformation functions representing a spatial transformation to the reference image from the diffusion weighted magnetic resonance images respectively corresponding to the first neural networks, and the first neural networks are configured to respectively provide first output images in response to the input of the reference image and the diffusion weighted magnetic resonance images respectively corresponding to the first neural networks; (iii) controlling the first output images to be input to a second neural network, in which the second neural network includes different second weights and the second neural network is configured to provide at least one second output image in response to the input of the first output images; (iv) providing third output images of which the number is the same as the number of first output images by applying intravoxel incoherent motion-diffusion kurtosis imaging (IVIM-DKI) to the reference image and the at least one second output image; (v) providing fourth output images by applying inverse functions of the transformation functions to the third output images; (vi) updating the first weights and the second weights by using the diffusion weighted magnetic resonance images, the first output images, the third output images, and the fourth output images; and (vii) repeating operations (ii) to (vi) a plurality of times.

The reference image may be a magnetic resonance imaging (MRI) image obtained in the setting of a b value to $0[s/mm^2]$, and the diffusion weighted magnetic resonance images may be MRI images obtained while changing a b value to different values except $0[s/mm^2]$.

As operation (vii) is performed, the first output images may get closer to the diffusion weighted magnetic resonance images and be closely registered with the reference image.

The diffusion weighted magnetic resonance images may be respectively generated by using diffusion weighted magnetic resonance images each obtained in a readout direction, in a phase encoding direction, and in a slice selection direction.

The at least one second output image may be a diffusion parameter image representing values of diffusion parameters on biometrics represented by the diffusion weighted magnetic resonance images.

The at least one second output image may include at least one of a diffusion coefficient image representing values of diffusion coefficients D on the biometrics represented by the diffusion weighted magnetic resonance images, a perfusion coefficient image representing values of perfusion coefficients $D_p$ on the biometrics represented by the diffusion weighted magnetic resonance images, a kurtosis image representing values of kurtoses K on the biometrics represented by the diffusion weighted magnetic resonance images, and a perfusion fraction image representing values of perfusion fractions f on the biometrics represented by the diffusion weighted magnetic resonance images.

As operation (vii) is performed, the third output images may get closer to the first output images.

As operation (vii) is performed, the fourth output images may get closer to the diffusion weighted magnetic resonance images.

Operation (vi) may include configuring a loss function by using the diffusion weighted magnetic resonance images, the first output images, the third output images, and the fourth output images and calculating the first weights and the second weights to minimize the loss function.

The loss function is defined by the following equations:

$$\text{loss} = \text{loss}_1 + \lambda \text{loss}_2$$
$$= \sum_b l_{NCC}\left(S_{in}(b); \hat{S}_{out}(b)\right) + \lambda \left\| S_a(b) - \hat{S}_a(b) \right\|$$
$$l_{NCC}(X; Y) = -\log\left(\frac{NCC(X; Y) + 1}{2}\right),$$

in which loss denotes the loss function, $\text{loss}_1$ denotes a first loss function, $\text{loss}_2$ denotes a second loss function, $S_{in}(b)$ denotes the diffusion weighted magnetic resonance images, $\hat{S}_{out}(b)$ denotes the fourth output images, $S_a(b)$ denotes the first output images, $\hat{S}_a(b)$ denotes the third output images, $\lambda$ denotes a weight, and NCC(X; Y) denotes a normalized cross correlation between X and Y.

According to embodiments, there is a technical effect of increasing the accuracy of quantifying magnetic resonance diffusion parameters.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the present disclosure will become apparent and more readily appreciated from the following description of example embodiments, taken in conjunction with the accompanying drawings of which.

DETAILED DESCRIPTION

Figure 1:
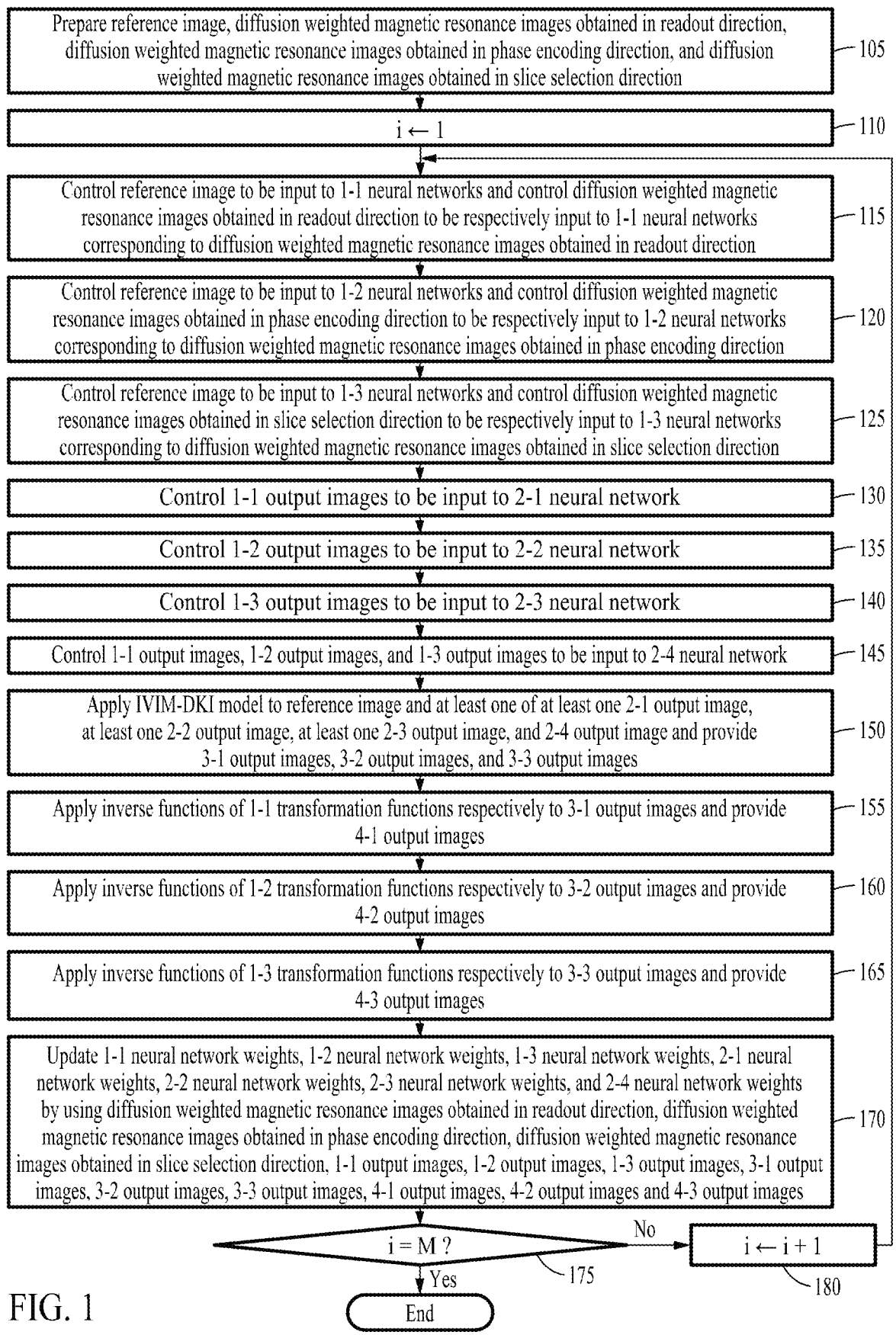
FIG. 1 is a flowchart illustrating a method of quantifying magnetic resonance diffusion parameters by using diffusion weighted magnetic resonance images, according to an embodiment.

The following detailed structural or functional description is provided as an example only and various alterations and modifications may be made to the examples. Here, the examples are not construed as limited to the disclosure and should be understood to include all changes, equivalents, and replacements within the idea and the technical scope of the disclosure.

Terms, such as "first", "second", and the like, may be used herein to describe components. Each of these terminologies is not used to define an essence, order or sequence of a corresponding component but used merely to distinguish the corresponding component from other component(s). For example, a "first" component may be referred to as a "second" component, or similarly, and the "second" component may be referred to as the "first" component within the scope of the right according to the concept of the present disclosure.

It should be noted that if it is described that one component is "connected", "coupled", or "joined" to another component, a third component may be "connected", "coupled", and "joined" between the first and second components, although the first component may be directly connected, coupled, or joined to the second component.

The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms used herein including technical or scientific terms have the same meaning as commonly understood by one of ordinary skill in the art to which examples belong. Terms, such as those defined in commonly used dictionaries, are to be interpreted as having a meaning that is consistent with their meaning in the context of the relevant art, and are not to be interpreted in an idealized or overly formal sense unless expressly so defined herein.

The present disclosure proposes an unsupervised deep learning method, which simultaneously performs registration between diffusion weighted magnetic resonance images and quantification of diffusion parameters. The unsupervised deep learning method may decrease a registration error caused by a contrast difference by comparing a similarity between images of the same contrast, increase the performance of registration, and increase the accuracy of quantifying magnetic resonance diffusion parameters. The unsupervised deep learning method may not require a large amount of data for learning. An economic effect may be expected because rescanning is not required even if patients move during a magnetic resonance imaging (MRI) scan. In addition, accurate quantification of diffusion parameters may assist diagnosing various diseases, such as cancer or a stroke, which may be diagnosed by using disease diffusion parameters.

Hereinafter, the examples are described in detail with reference to the accompanying drawings. When describing the examples with reference to the accompanying drawings, like reference numerals refer to like elements and a repeated description related thereto is omitted.

FIG. 1 is a flowchart illustrating a method of quantifying magnetic resonance diffusion parameters by using diffusion weighted magnetic resonance images, according to an embodiment, and FIGS. 2 to 11 are diagrams illustrating operations performed by the method described with reference to FIG. 1, according to an embodiment.

Referring to FIG. 1, the method of quantifying the magnetic resonance diffusion parameters may initiate with operation 105 of preparing a reference image $S_0$, diffusion weighted magnetic resonance images $S_{in}(b)$ obtained in a readout direction, diffusion weighted magnetic resonance images $S_{in}(b)$ obtained in a phase encoding direction, diffusion weighted magnetic resonance images $S_{in}(b)$ in obtained in a slice selection direction. The reference image $S_0$ may be an MRI image obtained in the setting of a b value, that is, a parameter set during an MRI scan, to $0[s/mm^2]$ The diffusion weighted magnetic resonance images $S_{in}(b)$ obtained in a readout direction, the diffusion weighted magnetic resonance images $S_{in}(b)$ obtained in a phase encoding direction, and the diffusion weighted magnetic resonance images $S_{in}(b)$ obtained in a slice selection direction may be MRI images obtained while changing the b value to different values except $0[s/mm^2]$. The diffusion weighted magnetic resonance images $S_{in}(b)$ obtained in a readout direction may be MRI images obtained while changing the b value and applying a diffusion gradient in left and right directions. The diffusion weighted magnetic resonance images $S_{in}(b)$ obtained in a phase encoding direction may be MRI images obtained while changing the b value and applying the diffusion gradient in forward and backward directions. The diffusion weighted magnetic resonance images $S_{in}(b)$ obtained in a slice selection direction may be MRI images obtained while changing the b value and applying the diffusion gradient in upward and downward directions. In operation 110, an index i indicating an iteration number may be initialized to 1.

Figure 2:
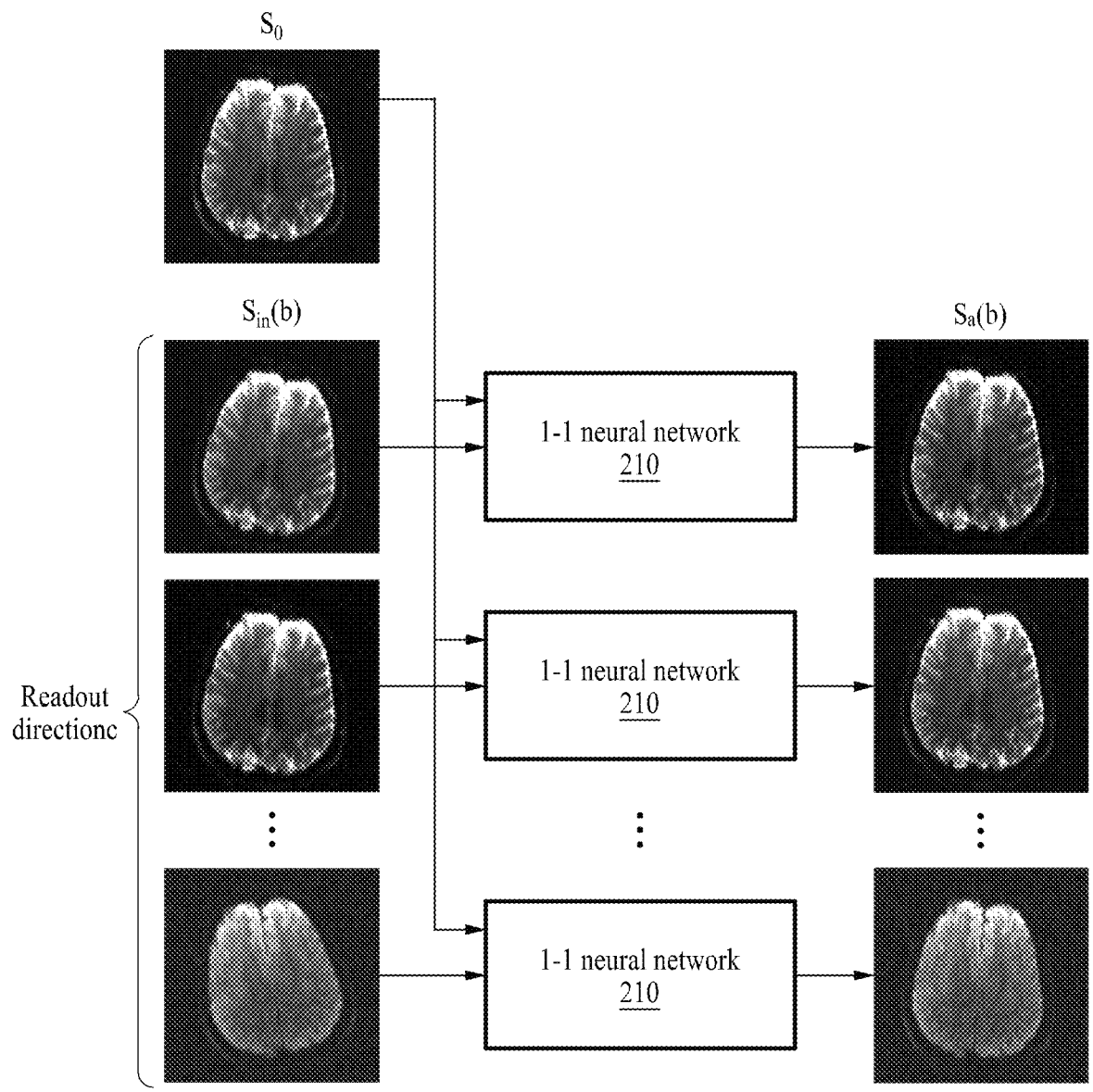
FIGS. 2 to 11 are diagrams illustrating operations performed by the method described with reference to FIG. 1, according to an embodiment.

In operation 115, as illustrated in FIG. 2, the reference image $S_0$ may be controlled to be input to 1-1 neural networks 210, and the diffusion weighted magnetic resonance images $S_{in}(b)$ obtained in a readout direction may be controlled to be respectively input to the 1-1 neural networks 210 respectively corresponding to the diffusion weighted magnetic resonance images $S_{in}(b)$ obtained in a readout direction. Each of the 1-1 neural networks 210 may include an input layer, hidden layers, and an output layer. Each of the hidden layers may include nodes. Nodes in the lowest hidden layer may be implemented to receive input vectors output from the input layer. Values of nodes in a relatively lower hidden layer may be transmitted to nodes in a relatively higher hidden layer after different 1-1 neural network weights are applied to the values. The output layer of the 1-1 neural network 210 may include nodes, to which the different 1-1 neural network weights are respectively applied, connected to nodes in the highest hidden layer. In an embodiment, the 1-1 neural network 210 may implement a deep neural network (DNN), a convolutional neural network (CNN), or a fully connected neural network (FCNN). The 1-1 neural networks 210 may be neural networks suitable for estimating a spatial transformation, such as parallel translation, scaling, shearing, rotation, and the like. In an embodiment, each of the 1-1 neural networks 210 may estimate a 1-1 transformation function representing a spatial transformation to the reference image $S_0$ from the diffusion weighted magnetic resonance image $S_{in}(b)$, corresponding to the 1-1 neural network 210, obtained in a readout direction. Each of the 1-1 neural networks 210 may provide a 1-1 output image $S_a(b)$ in response to the input of the reference image $S_0$ and the diffusion weighted magnetic resonance image ($S_{in}(b)$), corresponding to the 1-1 neural network 210, obtained in a readout direction.

Figure 3:
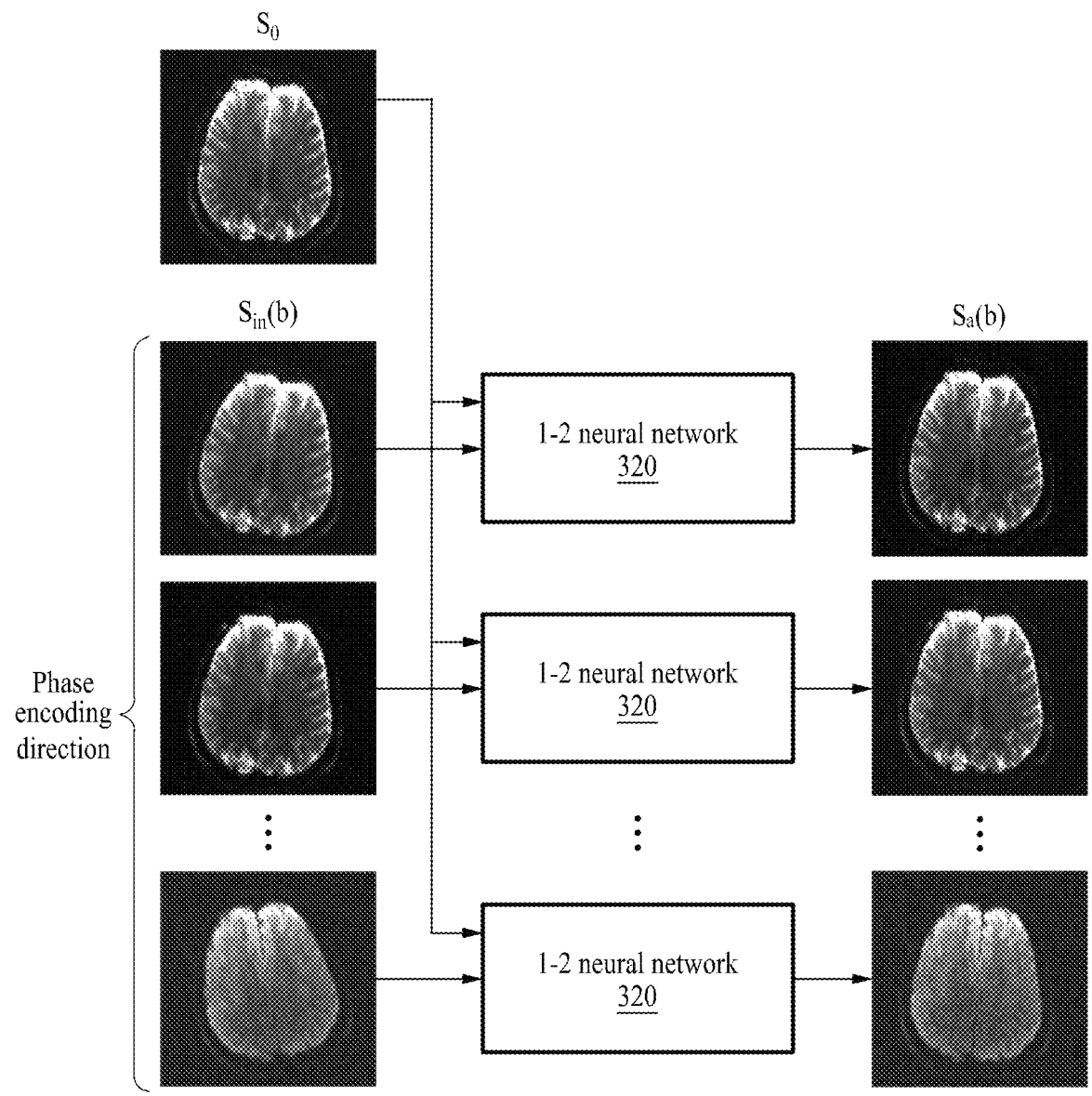

Referring to FIG. 1, in operation 120, as illustrated in FIG. 3, the reference image $S_0$ may be controlled to be input to 1-2 neural networks 320, and diffusion weighted magnetic resonance images $S_{in}(b)$ obtained in a phase encoding direction may be controlled to be respectively input to the 1-2 neural networks 320 respectively corresponding to the diffusion weighted magnetic resonance images $S_{in}(b)$ obtained in a phase encoding direction. The 1-2 neural networks 320 may respectively include different 1-2 neural network weights. The 1-2 neural networks 320 may be neural networks suitable for estimating a spatial transformation, such as parallel translation, scaling, shearing, rotation, and the like. In an embodiment, the 1-2 neural networks 320 may have the same structure as the 1-1 neural networks 210. In an embodiment, each of the 1-2 neural networks 320 may estimate a 1-2 transformation function representing a spatial transformation to the reference image $S_0$ from the diffusion weighted magnetic resonance image $S_{in}(b)$, corresponding to the 1-2 neural network 320, obtained in a phase encoding direction. Each of the 1-2 neural networks 320 may provide a 1-2 output image $S_a(b)$ response to the input of the reference image $S_0$ and the diffusion weighted magnetic resonance image $S_{in}(b)$, corresponding to the 1-2 neural network 320, obtained in a phase encoding direction.

Figure 4:
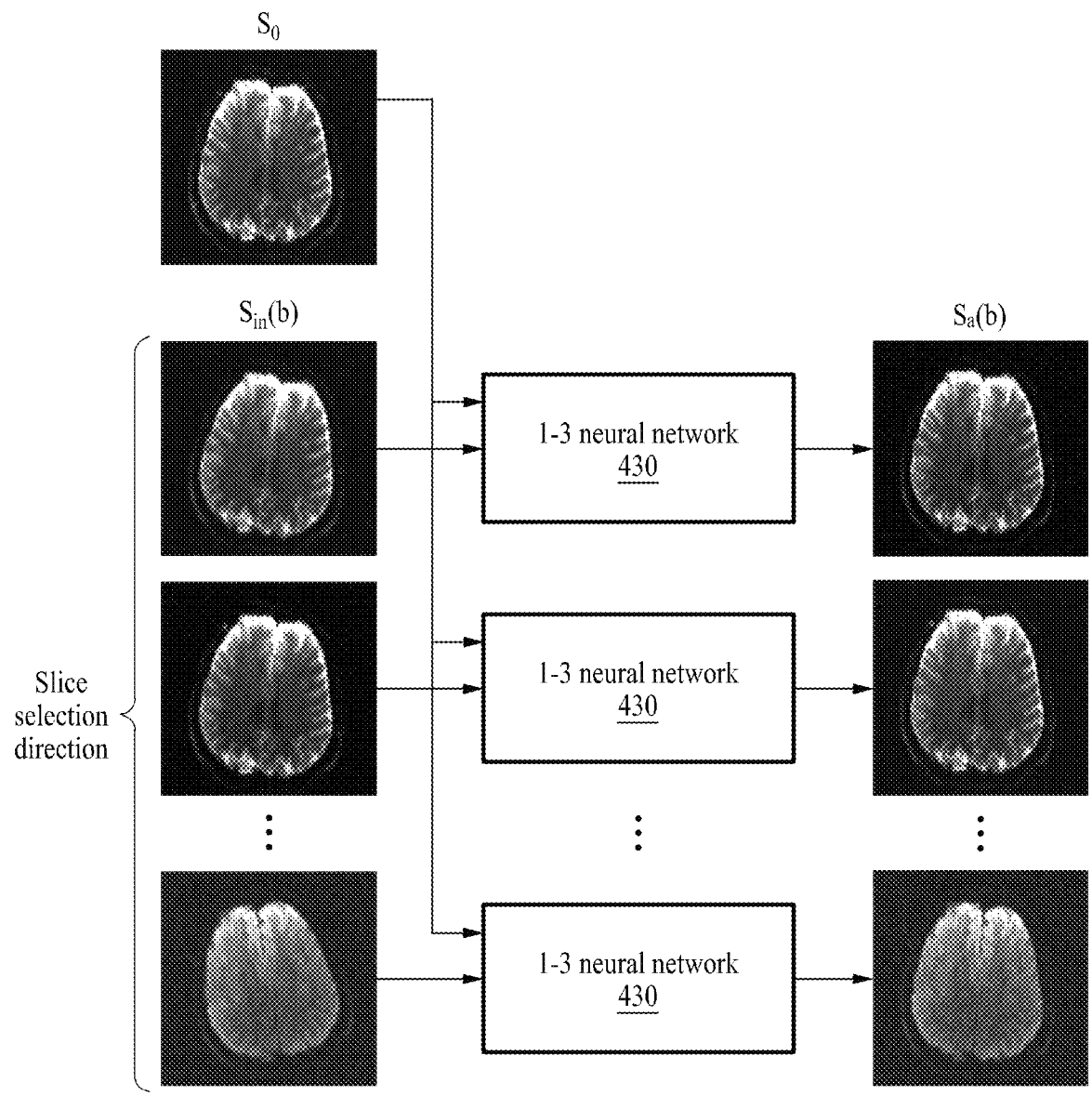

Referring to FIG. 1, in operation 125, as illustrated in FIG. 4, the reference image $S_0$ may be controlled to be input to 1-3 neural networks 430, and diffusion weighted magnetic resonance images $S_{in}(b)$ obtained in a slice selection direction may be controlled to be respectively input to the 1-3 neural networks 430 respectively corresponding to the diffusion weighted magnetic resonance images $S_{in}(b)$ obtained in a slice selection direction. The 1-3 neural networks 430 may respectively include different 1-3 neural network weights. The 1-3 neural networks 430 may be neural networks suitable for estimating a spatial transformation, such as parallel translation, scaling, shearing, rotation, and the like. In an embodiment, the 1-3 neural networks 430 may have the same structure as the 1-1 neural networks 210 and/or the 1-2 neural networks 320. In an embodiment, each of the 1-3 neural networks 430 may estimate a 1-3 transformation function representing a spatial transformation to the reference image $S_0$ from the diffusion weighted magnetic resonance image $S_{in}(b)$, corresponding to the 1-3 neural network 430, obtained in a slice selection direction. Each of the 1-3 neural networks 430 may provide a 1-3 output image $S_a(b)$ in response to the input of the reference image $S_0$ and the diffusion weighted magnetic resonance image $S_{in}(b)$, corresponding to the 1-3 neural network 430, obtained in a slice selection direction.

Although operations 115 to 125 are described above as separate operations, those skilled in the art will recognize that the operations may be performed practically at the same time. In addition, those skilled in the art will recognize that operations 115 to 125 may be performed in different orders. For example, those skilled in the art will recognize that operation 120 may be performed before operations 115 and 125. Accordingly, it should be understood and recognized that all such modified embodiments are within the scope of the present disclosure.

Figure 5:
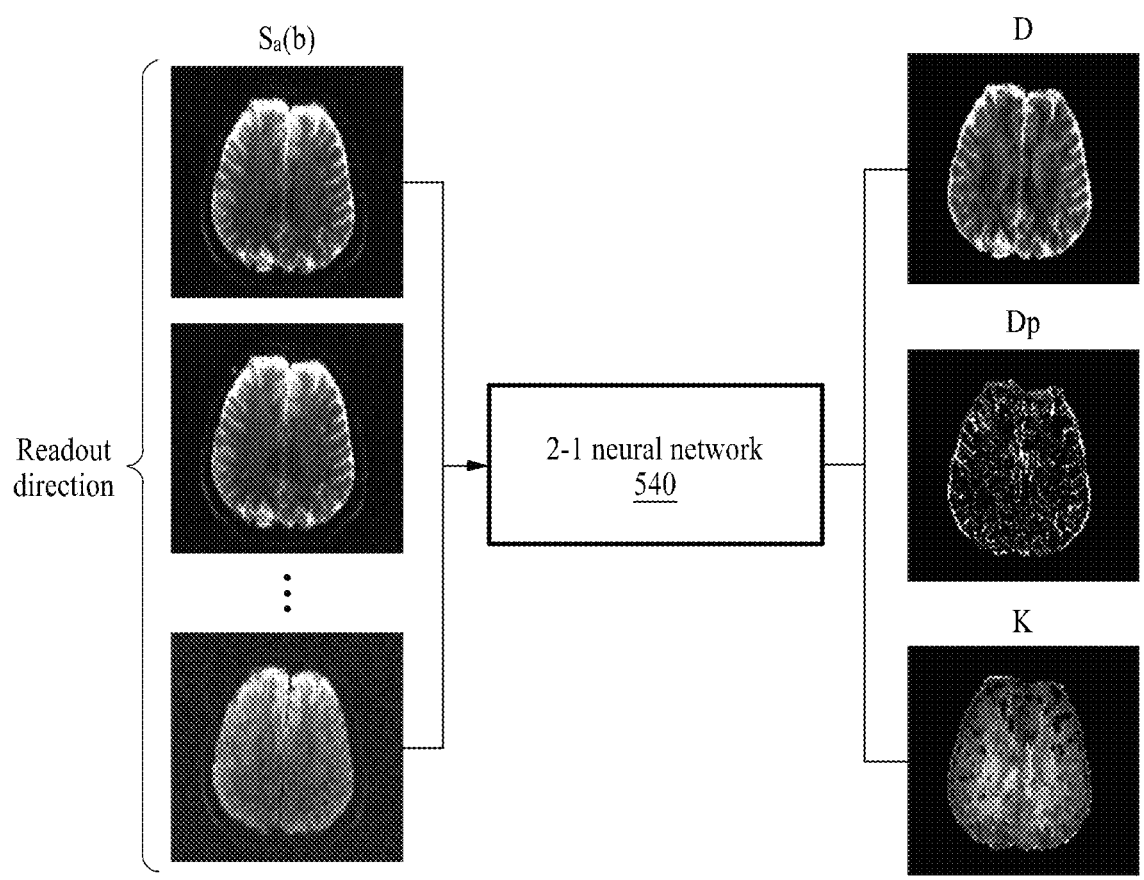

Referring to FIG. 1, in operation 130, as illustrated in FIG. 5, the 1-1 output images $S_a(b)$ may be controlled to be input to a 2-1 neural network 540. The 2-1 neural network 540 may be a neural network for quantifying diffusion parameters depending on at least one direction and may include different 2-1 neural network weights. The 2-1 neural network 540 may provide at least one 2-1 output image in response to the input of the 1-1 output images. The at least one 2-1 output image may include at least one of a diffusion coefficient image representing values of diffusion coefficients D on biometrics represented by the diffusion weighted magnetic resonance images $S_{in}(b)$ obtained in a readout direction, a perfusion coefficient image representing values of perfusion coefficients $D_p$ on the biometrics represented by the diffusion weighted magnetic resonance images $S_{in}(b)$ in obtained in a readout direction, and a kurtosis image representing values of kurtoses K on the biometrics represented by the diffusion weighted magnetic resonance images $S_{in}(b)$ in a readout direction.

Figure 6:
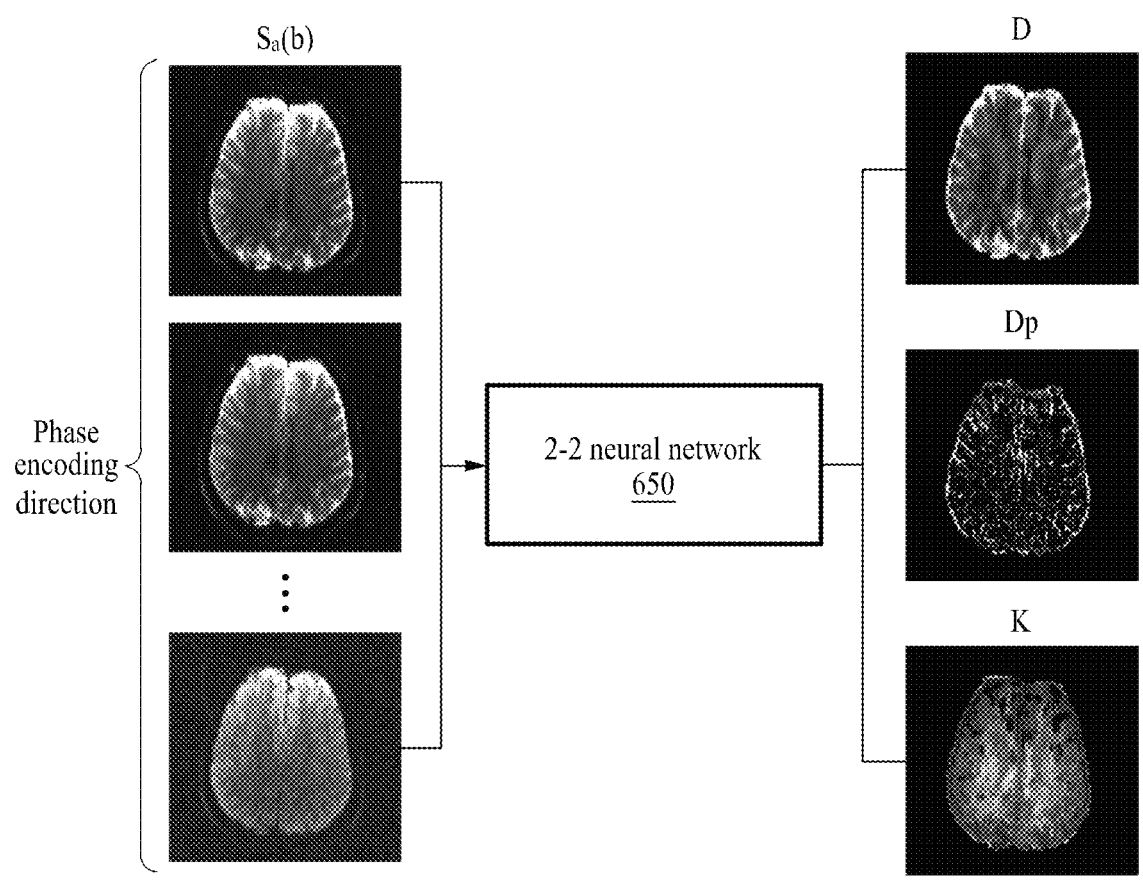

Referring to FIG. 1, in operation 135, as illustrated in FIG. 6, the 1-2 output images $S_a(b)$ may be controlled to be input to a 2-2 neural network 650. The 2-2 neural network 650 may be a neural network for quantifying diffusion parameters depending on at least one direction and may include different 2-2 neural network weights. In an embodiment, the 2-2 neural networks 650 may have the same structure as the 2-1 neural networks 540. The 2-2 neural network 650 may provide at least one 2-2 output image in response to the input of the 1-2 output images. The at least one 2-2 output image may include at least one of a diffusion coefficient image representing values of diffusion coefficients D on biometrics represented by the diffusion weighted magnetic resonance $S_{in}(b)$ obtained in a phase encoding direction, a perfusion coefficient image representing values of perfusion coefficients $D_p$ on the biometrics represented by the diffusion weighted magnetic resonance images $S_{in}(b)$ obtained in a phase encoding direction, and a kurtosis image representing values of kurtoses K on the biometrics represented by the diffusion weighted magnetic resonance images $S_{in}(b)$ in a phase encoding direction.

Figure 7:
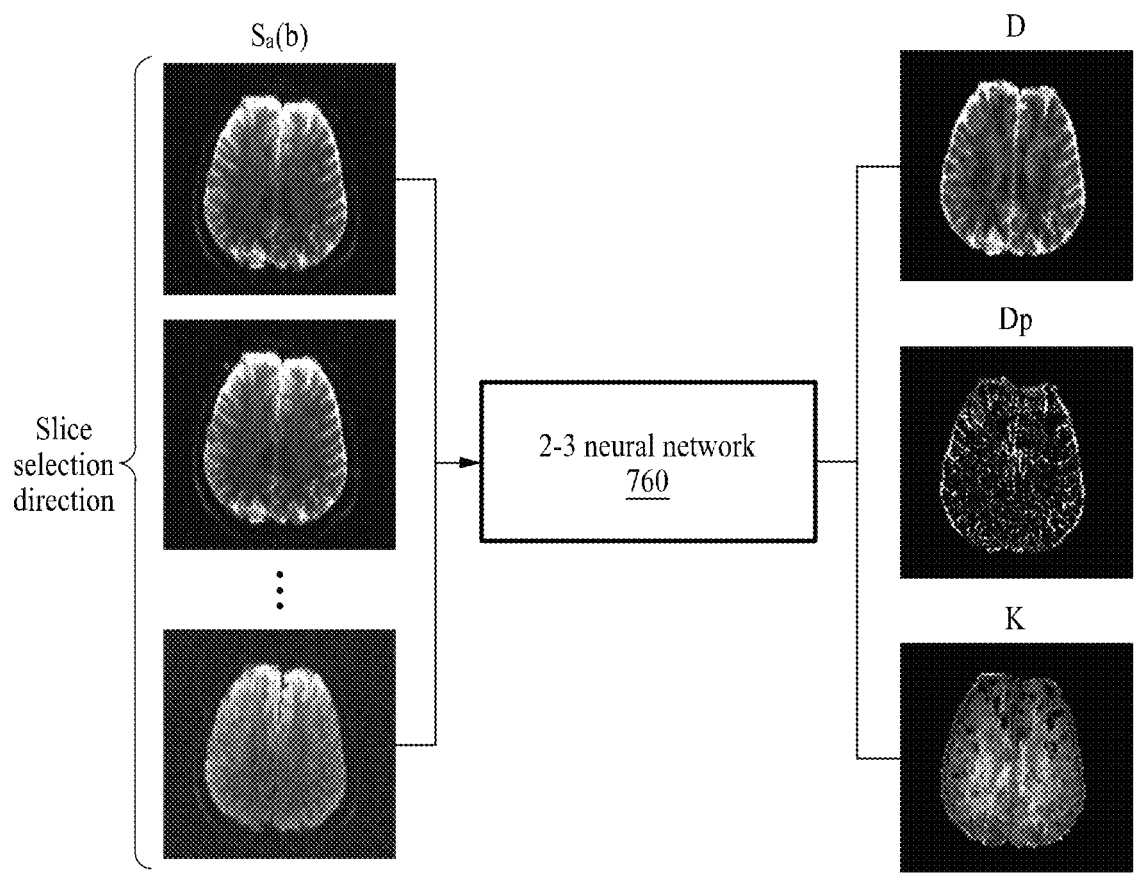

Referring to FIG. 1, in operation 140, as illustrated in FIG. 7, the 1-3 output images $S_a(b)$ may be controlled to be input to a 2-3 neural network 760. The 2-3 neural network 760 may be a neural network for quantifying diffusion parameters depending on at least one direction and may include different 2-3 neural network weights. In an embodiment, the 2-3 neural networks 760 may have the same structure as the 2-1 neural networks 540 and/or the 2-2 neural networks 650. The 2-3 neural network 760 may provide at least one 2-3 output image in response to the input of the 1-3 output images. The at least one 2-3 output image may include at least one of a diffusion coefficient image representing values of diffusion coefficients D on biometrics represented by the diffusion weighted magnetic resonance images $S_{in}(b)$ obtained in a slice selection direction, a perfusion coefficient image representing values of perfusion coefficients $D_p$ on the biometrics represented by the diffusion weighted magnetic resonance images $S_{in}(b)$ obtained in a slice selection direction, and a kurtosis image representing values of kurtoses K on the biometrics represented by the diffusion weighted magnetic resonance images $S_{in}(b)$ a slice selection direction.

Figure 8:
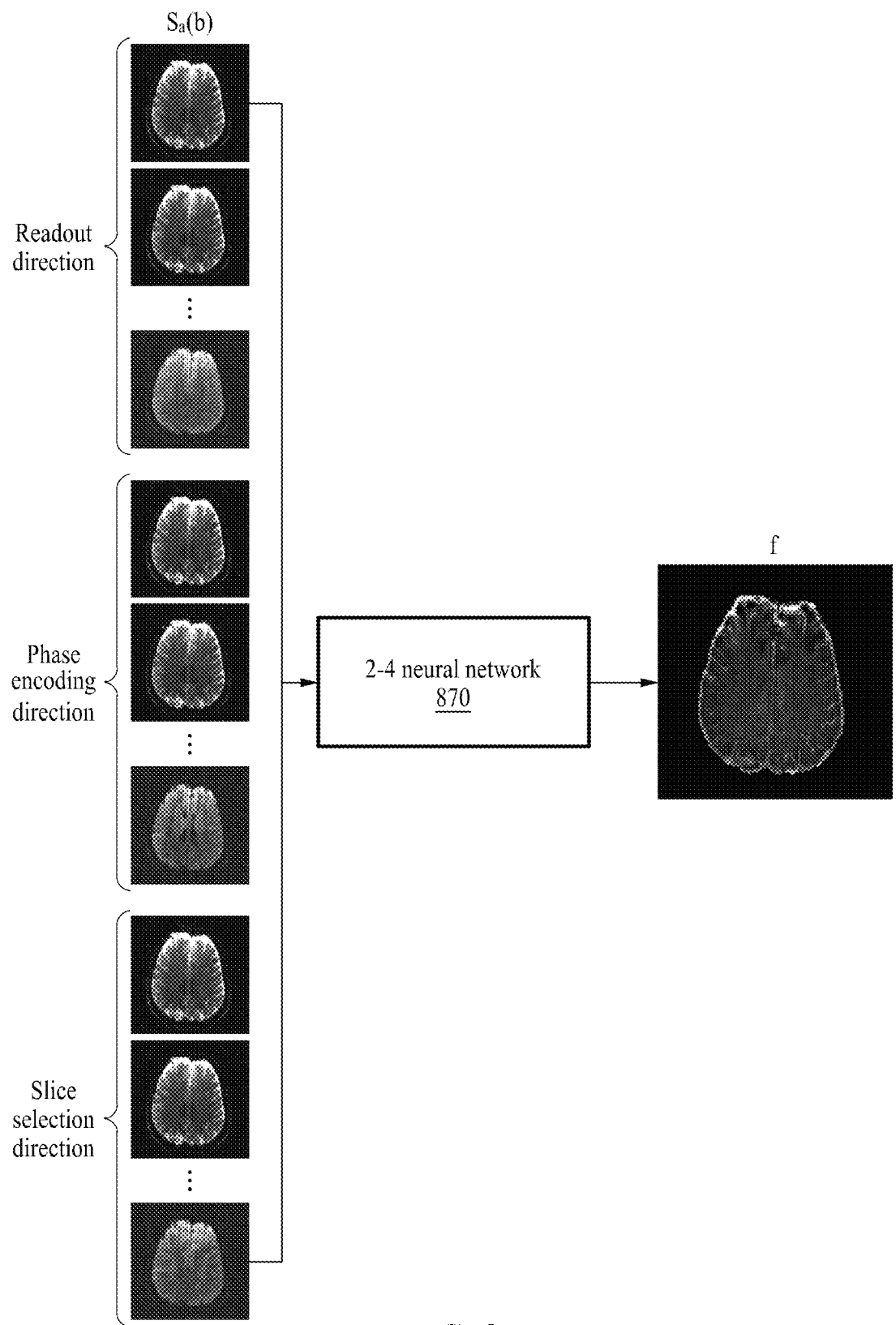

Referring to FIG. 1, in operation 145, as illustrated in FIG. 8, the 1-1 output images $S_a(b)$, the 1-2 output images $S_a(b)$, and the 1-3 output images $S_a(b)$ may be controlled to be input to a 2-4 neural network 870. The 2-4 neural network 870 may be a neural network for quantifying diffusion parameters not depending on a direction and may include different 2-4 neural network weights. The 2-4 neural network 870 may provide a 2-4 output image in response to the input of the 1-1 output images, 1-2 output images, and 1-3 output images. The 2-4 output image may be a perfusion fraction image representing values of perfusion fractions f on the biometrics represented by the diffusion weighted magnetic resonance images $S_{in}(b)$. Although the 1-1 output images $S_a(b)$, 1-2 output images $S_a(b)$ and 1-3 output images $S_a(b)$ are controlled to be respectively input to the 2-1 neural network 540, the 2-2 neural network 650, and the 2-3 neural network 760 in operations 130 to 140, the 1-1 output images $S_a(b)$, the 1-2 output images $S_a(b)$, and the 1-3 output images $S_a(b)$ may be controlled to be input to the 2-4 neural network 870 in operation 145 because the 2-1 neural network 540, the 2-2 neural network 650, and the 2-3 neural network 760 are neural networks for quantifying diffusion parameters depending on a direction, such as the diffusion coefficients D, the perfusion coefficients $D_p$, and the kurtoses k, but the 2-4 neural network 870 is a neural network for quantifying a diffusion parameter not depending on a direction, such as the perfusion fractions f.

Although operations 130 to 145 are described above as separate operations, those skilled in the art will recognize that the operations may be performed practically at the same time. In addition, those skilled in the art will recognize that operations 130 to 145 may be performed in different orders. For example, those skilled in the art will recognize that operation 145 may be performed before operations 130 to 140. Accordingly, it should be understood and recognized that all such modified embodiments are within the scope of the present disclosure.

Figure 9:
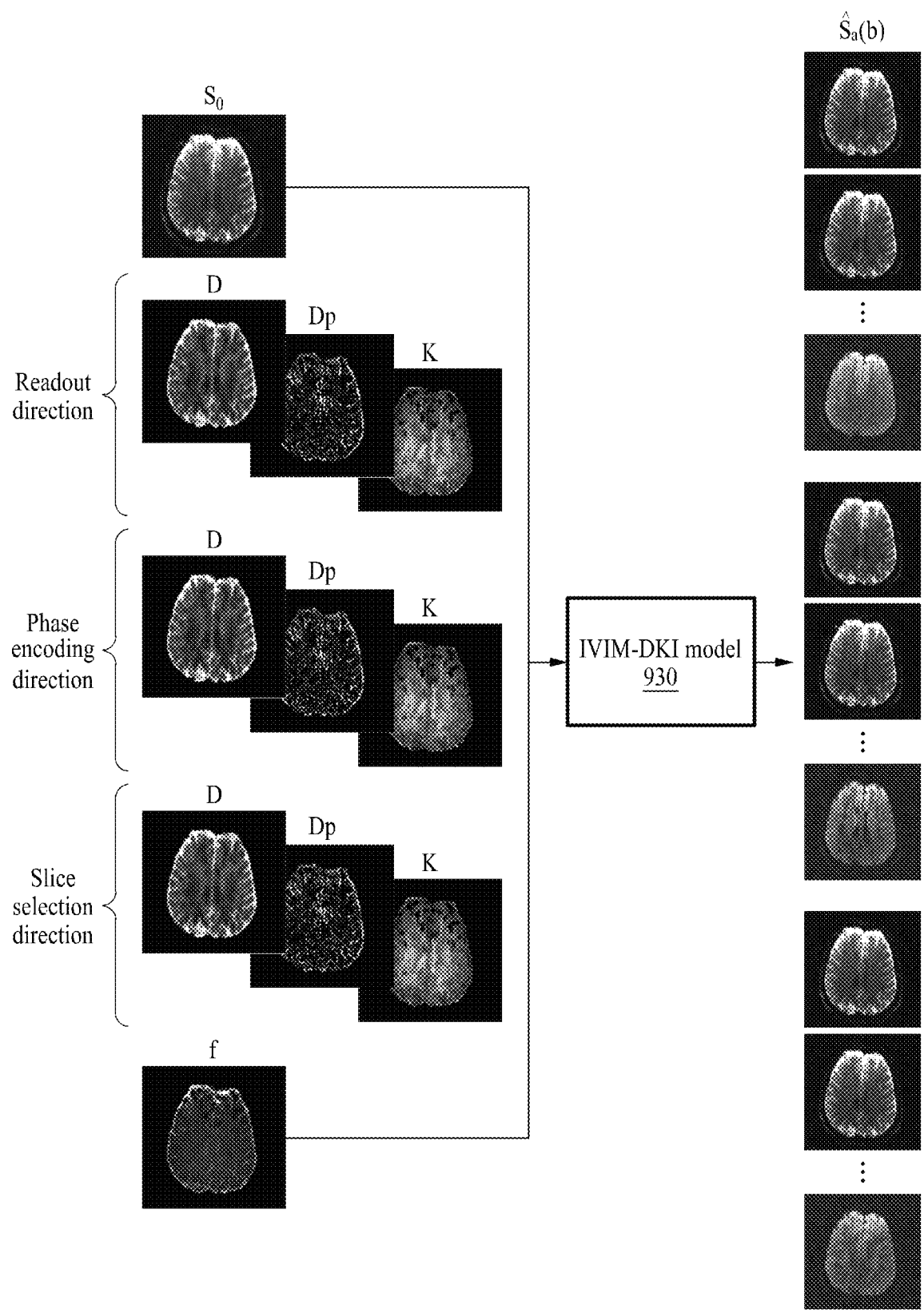

Referring to FIG. 1, in operation 150, as illustrated in FIG. 9, an intravoxel incoherent motion-diffusion kurtosis imaging (IVIM-DKI) model 930 may be applied to the reference image $S_0$ and at least one of at least one 2-1 output image, at least one 2-2 output image, at least one 2-3 output image, and the 2-4 output image, and 3-1 output images $\hat{S}_a(b)$ of which the number is the same as the number of 1-1 output images, 3-2 output images $\hat{S}_a(b)$ of which the number is the same as the number of 1-2 output images, and 3-3 output images $\hat{S}_a(b)$ of which the number is the same as the number of 1-3 output images may be provided. The IVIM-DKI model 930 may be expressed by Equation 1.

$$\hat{S}_a(b) = S_0(f^* \exp(-bD_p) + (1-f)^* \exp(-bD + \tfrac{1}{6} b^2 D^2 K)) \quad \text{[Equation 1]}$$

Here, $\hat{S}_a(b)$ denotes the 3-1 output images, the 3-2 output images, and the 3-3 output images, $S_0$ denotes a reference image, D denotes a diffusion coefficient image, $D_p$ denotes a perfusion coefficient image, K denotes a kurtosis image, f denotes a perfusion fraction image, b denotes b values used to obtain the diffusion weighted magnetic resonance images $S_{in}(b)$ obtained in a readout direction, the diffusion weighted magnetic resonance images $S_{in}(b)$ obtained in a phase encoding direction, or the diffusion weighted magnetic resonance images $S_{in}(b)$ obtained in a slice selection direction.

When the number of diffusion weighted magnetic resonance images $S_{in}(b)$ obtained in a readout direction, the number of diffusion weighted magnetic resonance images $S_{in}(b)$ obtained in a phase encoding direction, and the number of diffusion weighted magnetic resonance images $S_{in}(b)$ obtained in a slice selection direction each are N, the number of 3-1 output images $\hat{S}_a(b)$, the number of 3-2 output images $\hat{S}_a(b)$, and the number of 3-3 output images $\hat{S}_a(b)$ a may each be N. (b) In this case, for example, to provide N 3-1 output images $S_{in}(b)$, N b values used to obtain the diffusion weighted magnetic resonance images $S_{in}(b)$ obtained in N readout directions, the diffusion coefficient image D, the perfusion coefficient image $D_p$, the kurtosis image K, and the perfusion fraction image f, that is, at least one 2-1 output image, and the reference image $S_0$ may be used. In another example, to provide N 3-2 output images $\hat{S}_a(b)$, N b values used to obtain the diffusion weighted magnetic resonance images in $S_{in}(b)$ obtained in N phase encoding directions, the diffusion coefficient image D, the perfusion coefficient image $D_p$, the kurtosis image K, and the perfusion fraction image f, that is, at least one 2-2 output image, and the reference image $S_0$ may be used. Yet another example, to provide N 3-3 output images $\hat{S}_a(b)$, N b values used to obtain the diffusion weighted magnetic resonance images $S_{in}(b)$ obtained in N slice selection directions, the diffusion coefficient image D, the perfusion coefficient image $D_p$, the kurtosis image K, and the perfusion fraction image f, that is, at least one 2-3 output image, and the reference image $S_0$ may be used.

Figure 10:
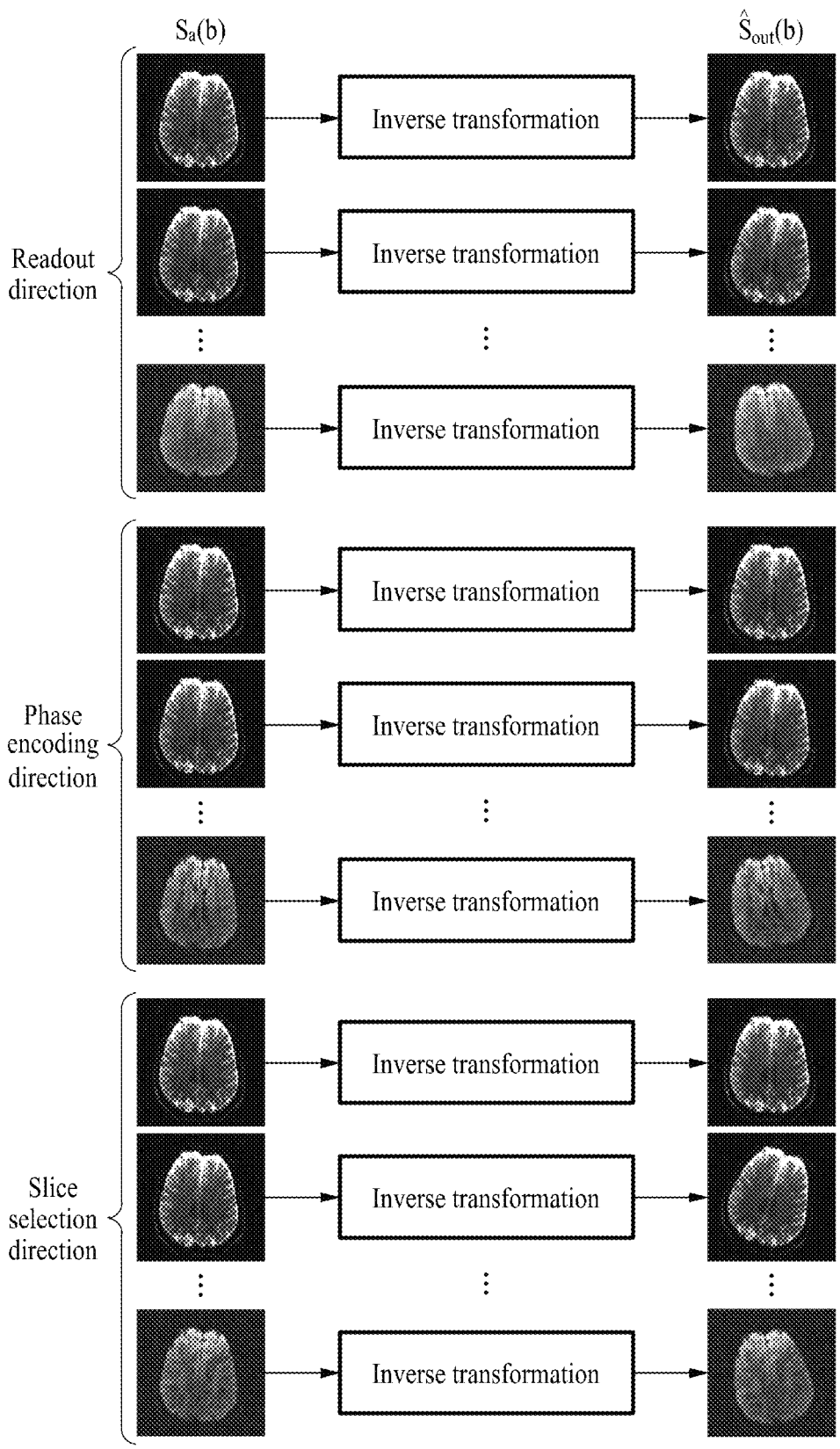

Referring to FIG. 1, in operations 155 to 165, as illustrated in FIG. 10, the 3-1 output images $\hat{S}_a(b)$, the 3-2 output images $\hat{S}_a(b)$, and the 3-3 output images $\hat{S}_a(b)$ may respectively be inversely transformed and 4-1 output images $\hat{S}_{out}(b)$, 4-2 output images $\hat{S}_{out}(b)$, and 4-3 output images $\hat{S}_{out}(b)$ may be provided. Specifically, in operation 155, as illustrated in FIG. 10, inverse functions of the 1-1 transformation functions provided in operation 115 may be respectively applied to the 3-1 output images $\hat{S}_a(b)$, and the 4-1 output images $\hat{S}_{out}(b)$ may be provided. In operation 160, as illustrated in FIG. 10, inverse functions of the 1-2 transformation functions provided in operation 120 may be respectively applied to the 3-2 output images $\hat{S}_a(b)$, and the 4-2 output images $\hat{S}_{out}(b)$ may be provided. In operation 165, as illustrated in FIG. 10, inverse functions of the 1-3 transformation functions provided in operation 125 may be respectively applied to the 3-3 output images $\hat{S}_a(b)$, and the 4-3 output images out $\hat{S}_{out}(b)$ may be provided. Those skilled in the art will understand that operations 155, 160, and 165 may be performed at the same time or in different orders.

Figure 11:
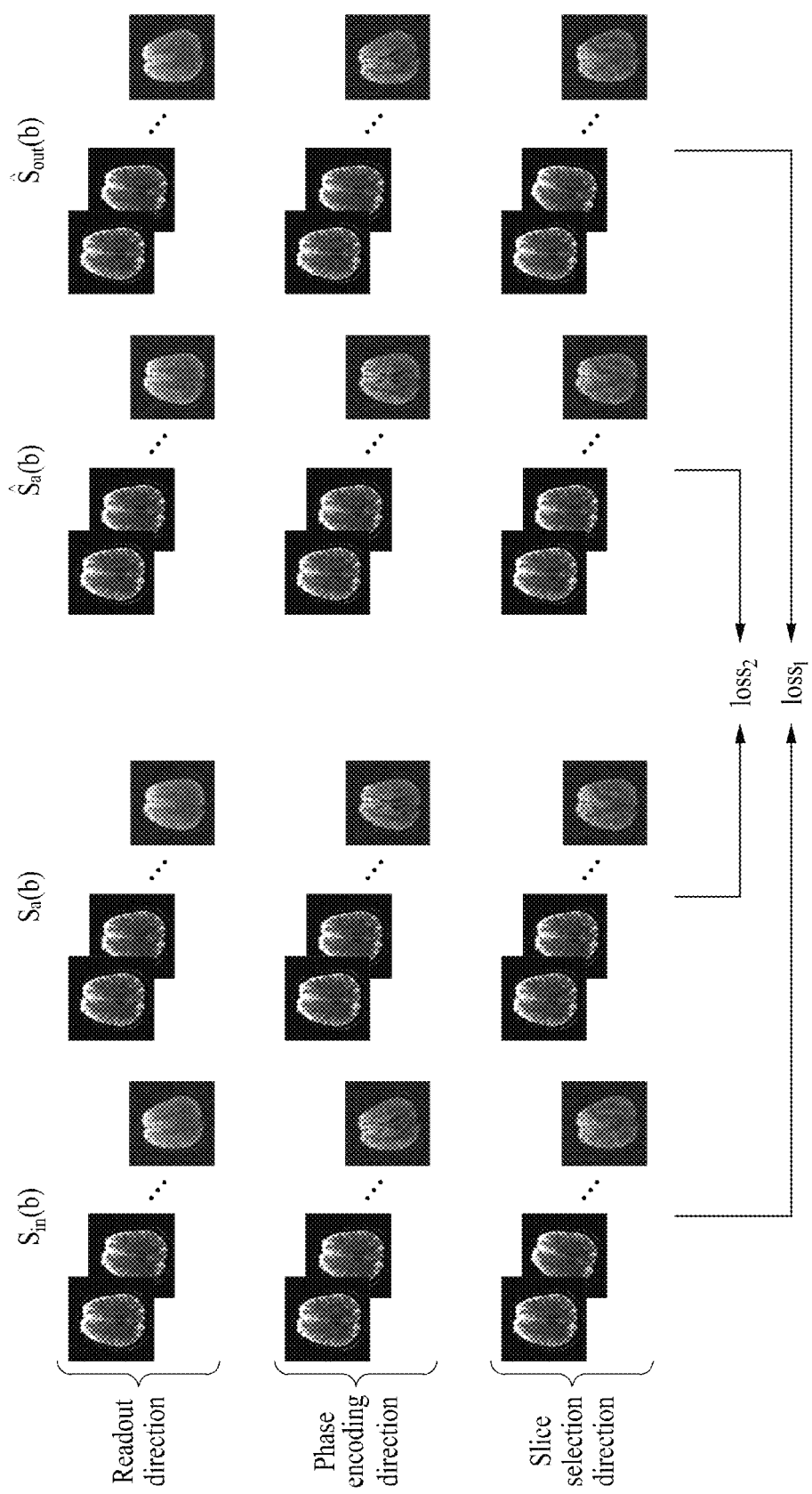

Referring to FIG. 1, in operation 170, as illustrated in FIG. 11, the 1-1 neural network weights, the 1-2 neural network weights, the 1-3 neural network weights, the 2-1 neural network weights, the 2-2 neural network weights, the 2-3 neural network weights, and the 2-4 neural network weights may be updated by using the diffusion weighted magnetic resonance images $S_{in}(b)$ obtained in a readout direction, the diffusion weighted magnetic resonance images $S_{in}(b)$ obtained in a phase encoding direction, the diffusion weighted magnetic resonance images $S_a(b)$ obtained in a slice selection direction, the 1-1 output images $S_a(b)$, the 1-2 output images $\hat{S}_a(b)$, the 1-3 output images $S_a(b)$, the 3-1 output images $\hat{S}_a(b)$, the 3-2 output images $\hat{S}_a(b)$, the 3-3 output images $\hat{S}_a(b)$, the 4-1 output images $\hat{S}_{out}(b)$, the 4-2 output images $\hat{S}_{out}(b)$ and the 4-3 output images $\hat{S}_{out}(b)$. In operation 170, a loss function may be configured by using the diffusion weighted magnetic resonance images $S_{in}(b)$ obtained in a readout direction, the diffusion weighted magnetic resonance images $S_{in}(b)$ obtained in a phase encoding direction, the diffusion weighted magnetic resonance images $S_{in}(b)$ obtained in a slice selection direction, the 1-1 output images $S_a(b)$, the 1-2 output images $S_a(b)$, the 1-3 output images $S_a(b)$, the 3-1 output images $\hat{S}_a(b)$, the 3-2 output images $\hat{S}_a(b)$ the 3-3 output images $\hat{S}_a(b)$, the 4-1 output images $\hat{S}_{out}(b)$, the 4-2 output images $\hat{S}_{out}(b)$, and the 4-3 output images $\hat{S}_{out}(b)$. In operation 170, the 1-1 neural network weights, the 1-2 neural network weights, the 1-3 neural network weights, the 2-1 neural network weights, the 2-2 neural network weights, the 2-3 neural network weights, and the 2-4 neural network weights may be updated by calculating the 1-1 neural network weights, the 1-2 neural network weights, the 1-3 neural network weights, the 2-1 neural network weights, the 2-2 neural network weights, the 2-3 neural network weights, and the 2-4 neural network weights for minimizing the loss function. In an embodiment, the loss function defined by Equations 2 and 3 may be used to update neural network weights.

$$\text{loss} = \text{loss}_1 + \lambda \text{loss}_2 \quad \text{[Equation 2]}$$
$$= \sum_b l_{NCC}(S_{in}(b); \hat{S}_{out}(b)) + \lambda \|S_a(b) - \hat{S}_a(b)\|$$
$$l_{NCC}(X; Y) = -\log\left(\frac{NCC(X;Y)+1}{2}\right) \quad \text{[Equation 3]}$$

In the above equations, loss denotes the loss function, $\text{loss}_1$ denotes a first loss function, $\text{loss}_2$ denotes a second loss function, $S_{in}(b)$ denotes the diffusion weighted magnetic resonance images obtained in a readout direction, the diffusion weighted magnetic resonance images obtained in a phase encoding direction, and the diffusion weighted magnetic resonance images obtained in a slice selection direction, $\hat{S}_{out}(b)$ denotes the 4-1 output images, the 4-2 output images, and the 4-3 output images, $S_a(b)$ denotes the 1-1 output images, the 1-2 output images, and the 1-3 output images, $\hat{S}_a(b)$ a denotes the 3-1 output images, the 3-2 output images, and the 3-3 output images, $\lambda$ denotes a neural network weight, and NCC (X; Y) denotes a normalized cross correlation between X and Y.

Referring to FIG. 1, in operation 175, the index i indicating an iteration number may be verified as to whether the index is M (here, M is a natural number greater than or equal to 2). When i is determined to be M as a result of the verification in operation 175, a process may be terminated. When i is determined not to be M as the result of the verification in operation 175, the process may continue to operation 180, in which i may increase by 1, and may return to operation 115. In the illustrated embodiments, the 1-1 neural networks 210, the 1-2 neural networks 320, the 1-3 neural networks 430, the 2-1 neural network 540, the 2-2 neural network 650, the 2-3 neural network 760, and the 2-4 neural network 870 may be repeatedly trained for a certain number M of times. Because the loss function is closer to a minimum value as M increases, the 1-1 neural networks 210, the 1-2 neural networks 320, the 1-3 neural networks 430, the 2-1 neural network 540, the 2-2 neural network 650, the 2-3 neural network 760, and the 2-4 neural network 870 may be better trained as M increases. However, an excessive number of repetitions may overload a processor. To decrease a load on the processor, the number of repetitions may be limited to a selected number of times or a timeout may be set in a processing time.

When the training is performed as above, the 1-1 output images $S_a(b)$ may respectively get closer to the diffusion weighted magnetic resonance images $S_{in}(b)$ obtained in a readout direction and be closely registered with the reference image $S_0$. When the training is performed as above, the 1-2 output images a $S_{in}(b)$ may respectively get closer to the diffusion weighted magnetic resonance images $S_{in}(b)$ obtained in a phase encoding direction and be closely registered with the reference image $S_0$. When the training is performed as above, the 1-3 output images $S_a(b)$ may respectively get closer to the diffusion weighted magnetic resonance images $S_{in}(b)$ obtained in a slice selection direction and be closely registered with the reference image $S_0$. When the training is performed as above, the 3-1 output images $\hat{S}_a(b)$ may respectively get closer to the 1-1 output images $S_a(b)$. When the training is performed as above, the 3-2 output images $\hat{S}_a(b)$ may respectively get closer to the 1-2 output images $S_a(b)$. When the training is performed as above, the 3-3 output images $\hat{S}_a(b)$ may respectively get closer to the 1-3 output images $S_a(b)$. When the training is performed as above, the 4-1 output images $\hat{S}_{out}(b)$ may respectively get closer to the diffusion weighted magnetic resonance images $S_{in}(b)$ obtained in a readout direction. When the training is performed as above, the 4-2 output images $\hat{S}_{out}(b)$ may respectively get closer to the diffusion weighted magnetic resonance images $S_{in}(b)$ obtained in a phase encoding direction. When the training is performed as above, the 4-3 output images $\hat{S}_{out}(b)$ may respectively get closer to the diffusion weighted magnetic resonance images $S_{in}(b)$ obtained in a slice selection direction. When the training is performed as above, at least one 2-1 output image, at least one 2-2 output image, at least one 2-3 output image, and at least one 2-4 output image may better represent values of diffusion parameters on the biometrics represented by the diffusion weighted magnetic resonance images $S_{in}(b)$.

Although a method of inputting the diffusion weighted magnetic resonance images $S_{in}(b)$ obtained in a readout direction, the diffusion weighted magnetic resonance images $S_{in}(b)$ obtained in a phase encoding direction, the diffusion weighted magnetic resonance images $S_{in}(b)$ obtained in a slice selection direction all to the neural networks and simultaneously performing the registration of the images and the quantification of diffusion parameters is described above, it should be recognized that the present disclosure is not limited to the foregoing examples. In some embodiments, the diffusion weighted magnetic resonance images $S_{in}(b)$ obtained in a readout direction, the diffusion weighted magnetic resonance images $S_{in}(b)$ obtained in a phase encoding direction, and the diffusion weighted magnetic resonance images $S_{in}(b)$ obtained in a slice selection direction may be combined to generate combined images. The combined images may be input to the neural networks, and the registration of the combined images and the quantification of diffusion parameters may be performed. In some embodiments, the combined images may respectively be an averaged diffusion weighted magnetic resonance image $S_{in}(b)$ obtained in a readout direction, an averaged diffusion weighted magnetic resonance image $S_{in}(b)$ obtained in a phase encoding direction, and an averaged diffusion weighted magnetic resonance image $S_{in}(b)$ obtained n a slice selection direction.

The examples described herein may be implemented using a hardware component, a software component and/or a combination thereof. A processing device may be implemented using one or more general-purpose or special-purpose computers, such as, for example, a processor, a controller and an arithmetic logic unit (ALU), a digital signal processor (DSP), a microcomputer, a field programmable gate array (FPGA), a programmable logic unit (PLU), a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciate that a processing device may include multiple processing elements and multiple types of processing elements. For example, the processing device may include a plurality of processors, or a single processor and a single controller. In addition, different processing configurations are possible, such as parallel processors.

The software may include a computer program, a piece of code, an instruction, or some combination thereof, to independently or uniformly instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network-coupled computer systems so that the software is stored and executed in a distributed fashion. The software and data may be stored by one or more non-transitory computer-readable recording mediums.

The methods according to the above-described examples may be recorded in non-transitory computer-readable media including program instructions to implement various operations of the above-described examples. The media may also include, alone or in combination with the program instructions, data files, data structures, and the like. The program instructions recorded on the media may be those specially designed and constructed for the purposes of examples, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher-level code that may be executed by the computer using an interpreter.

The above-described devices may act as one or more software modules in order to perform the operations of the above-described examples, or vice versa.

As described above, although the examples have been described with reference to the limited drawings, a person skilled in the art may apply various technical modifications and variations based thereon. For example, suitable results may be achieved if the described techniques are performed in a different order and/or if components in a described system, architecture, device, or circuit are combined in a different manner and/or replaced or supplemented by other components or their equivalents.

Accordingly, other implementations are within the scope of the following claims.

What is claimed is:

1. A method of quantifying magnetic resonance diffusion parameters, as a method of quantifying the magnetic resonance diffusion parameters by using diffusion weighted magnetic resonance images, the method comprising:
   (i) preparing a reference image and diffusion weighted magnetic resonance images;
   (ii) controlling the reference image to be input to first neural networks and the diffusion weighted magnetic resonance images to be respectively input to the first neural networks, wherein the first neural networks are configured to estimate transformation functions representing a spatial transformation to the reference image from the diffusion weighted magnetic resonance images respectively corresponding to the first neural networks, and the first neural networks are configured to respectively provide first output images in response to the input of the reference image and the diffusion weighted magnetic resonance images respectively corresponding to the first neural networks;
   (iii) controlling the first output images to be input to second neural networks, wherein the second neural networks are configured to provide at least one second output image in response to the input of the first output images;
   (iv) providing third output images of which the number is the same as the number of first output images by applying intravoxel incoherent motion-diffusion kurtosis imaging (IVIM-DKI) to the reference image and the at least one second output image;
   (v) providing fourth output images by applying inverse functions of the transformation functions to the third output images;
   (vi) updating the first and second neural networks by using the diffusion weighted magnetic resonance images, the first output images, the third output images, and the fourth output images; and
   (vii) repeating operations (ii) to (vi) a plurality of times, wherein, the first neural networks include one or more neural networks, each of which is distinguished based on the direction of diffusion gradient and the second neural networks include one or more neural networks, each of which is for quantifying diffusion parameters.

2. The method of claim 1, wherein
the reference image is a magnetic resonance imaging (MRI) image obtained in the setting of a b value to 0[s/mm$^2$], and
the diffusion weighted magnetic resonance images are MRI images obtained while changing a b value to different values except 0[s/mm$^2$].

3. The method of claim 1, wherein,
as operation (vii) is performed, the first output images get closer to the diffusion weighted magnetic resonance images and closely registered with the reference image.

4. The method of claim 1, wherein
the diffusion weighted magnetic resonance images are respectively generated by using diffusion weighted magnetic resonance images each obtained in a readout direction, in a phase encoding direction, and in a slice selection direction.

5. The method of claim 1, wherein
the at least one second output image is a diffusion parameter image representing values of diffusion parameters on biometrics represented by the diffusion weighted magnetic resonance images.

6. The method of claim 5, wherein
the at least one second output image comprises at least one of:
a diffusion coefficient image representing values of diffusion coefficients D on the biometrics represented by the diffusion weighted magnetic resonance images;
a perfusion coefficient image representing values of perfusion coefficients $D_p$ on the biometrics represented by the diffusion weighted magnetic resonance images;
a kurtosis image representing values of kurtoses K on the biometrics represented by the diffusion weighted magnetic resonance images; and
a perfusion fraction image representing values of perfusion fractions f on the biometrics represented by the diffusion weighted magnetic resonance images.

7. The method of claim 1, wherein, as operation (vii) is performed, the third output images get closer to the first output images.

8. The method of claim 1, wherein, as operation (vii) is performed, the fourth output images get closer to the diffusion weighted magnetic resonance images.

9. The method of claim 1, wherein:
updating the first and second neural networks includes:
configuring a loss function by using the diffusion weighted magnetic resonance images, the first output images, the third output images, and the fourth output images; and calculating the first weights and the second weights to minimize the loss function,
the first weights include one or more neural network weights related to the first neural works, and
the second weights include one or more neural network weights related to the second neural networks.

10. The method of claim 9, wherein
the loss function is defined by the following equations:

$$\mathrm{loss} = \mathrm{loss}_1 + \lambda \mathrm{loss}_2$$
$$= \sum_b l_{NCC}\left(S_{in}(b); \hat{S}_{out}(b)\right) + \lambda \left\| S_a(b) - \hat{S}_a(b) \right\|$$
$$l_{NCC}(X; Y) = -\log\left(\frac{NCC(X; Y) + 1}{2}\right),$$

wherein loss denotes the loss function, loss$_1$ denotes a first loss function, loss$_2$ denotes a second loss function, $S_{in}(b)$ denotes the diffusion weighted magnetic resonance images, $\hat{S}_{out}(b)$ denotes the fourth output images, $S_a(b)$ denotes the first output images, $\hat{S}_a(b)$ denotes the third output images, $\lambda$ denotes a weight, and NCC(X; Y) denotes a normalized cross correlation between X and Y.

* * * * *